(12) United States Patent
Jones et al.

(10) Patent No.: US 7,108,976 B2
(45) Date of Patent: Sep. 19, 2006

(54) COMPLEXITY MANAGEMENT OF GENOMIC DNA BY LOCUS SPECIFIC AMPLIFICATION

(75) Inventors: Keith W. Jones, Sunnyvale, CA (US); Michael Shapero, Redwood City, CA (US); Weiwei Liu, Menlo Park, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/272,155

(22) Filed: Oct. 14, 2002

(65) Prior Publication Data

US 2003/0232348 A1 Dec. 18, 2003

Related U.S. Application Data

(60) Provisional application No. 60/389,747, filed on Jun. 17, 2002.

(51) Int. Cl.
*C12Q 1/68* (2006.01)
*C12P 19/34* (2006.01)

(52) U.S. Cl. .......................... 435/6; 435/91.1; 435/91.2
(58) Field of Classification Search .................. 435/6, 435/91.1, 91.2; 536/24.3, 24.33
See application file for complete search history.

(56) References Cited

U.S. PATENT DOCUMENTS

| | | | |
|---|---|---|---|
| 5,002,867 A | | 3/1991 | Macevicz |
| 5,143,854 A | | 9/1992 | Pirrung et al. |
| 5,202,231 A | | 4/1993 | Drmanac et al. |
| 5,387,505 A | * | 2/1995 | Wu .............................. 435/6 |
| 5,492,806 A | | 2/1996 | Drmanac et al. |
| 5,508,169 A | | 4/1996 | Deugau et al. |
| 5,580,730 A | * | 12/1996 | Okamoto ..................... 435/6 |
| 5,582,989 A | | 12/1996 | Caskey et al. |
| 5,624,825 A | | 4/1997 | Walker et al. |
| 5,667,972 A | | 9/1997 | Drmanac et al. |
| 5,695,940 A | | 12/1997 | Drmanac et al. |
| 5,700,637 A | | 12/1997 | Southern |
| 5,700,642 A | * | 12/1997 | Monforte et al. ............. 435/6 |
| 5,710,000 A | | 1/1998 | Sapolsky et al. |
| 5,776,753 A | * | 7/1998 | Hillman et al. ............. 435/196 |
| 5,854,033 A | * | 12/1998 | Lizardi ....................... 435/91.2 |
| 5,994,068 A | | 11/1999 | Guilfoyle et al. |
| 6,197,510 B1 | | 3/2001 | Vinayagamoorthy |
| 6,232,066 B1 | * | 5/2001 | Felder et al. .................. 435/6 |
| 6,258,539 B1 | | 7/2001 | Hunkapiller et al. |
| 6,280,950 B1 | * | 8/2001 | Lipshutz et al. ............... 435/6 |
| 6,322,971 B1 | * | 11/2001 | Chetverin et al. ............ 435/6 |
| 6,355,431 B1 | | 3/2002 | Chee et al. |
| 6,361,947 B1 | | 3/2002 | Dong et al. |
| 6,720,179 B1 | | 4/2004 | Macevicz |
| 6,773,885 B1 | | 8/2004 | Walder et al. |
| 6,773,886 B1 | | 8/2004 | Kaufman et al. |
| 6,812,005 B1 | * | 11/2004 | Fan et al. .................... 435/91.2 |
| 2003/0036069 A1 | | 2/2003 | Su |

FOREIGN PATENT DOCUMENTS

| | | |
|---|---|---|
| EP | 1350853 A1 | 10/2003 |
| WO | WO/01/88174 A1 | 11/2001 |

OTHER PUBLICATIONS

Natalia E. Broude et al; High Level Multiplex DNA Amplification; Antisense & Nucleic Acid Drug Development 11:327-332 (2001).
Natalia E. Broude et al; Multiplex Allele-Specific Target Amplification Based on PCR Suppression; PNA, Jan. 2, 2001: Vo. 98. No. 1; 206-211.
Paul D. Siebert et al; An Improved PCR Method for Walking an Uncloned Genomic DNA; Nucleic Acids Research, 1995; Vo. 23 No. 6; 1087-1088.

* cited by examiner

*Primary Examiner*—Young J. Kim
(74) *Attorney, Agent, or Firm*—Sandra E. Wells

(57) ABSTRACT

The present invention provides for novel methods and kits for reducing the complexity of a nucleic acid sample to interrogate a collection of target sequences. In one embodiment complexity reduction can be accomplished by extension of a locus specific capture probe followed by amplification of the extended capture probe using common primers. The locus specific capture probes may be attached to a solid support. Multiple DNA sequences may be amplified simultaneously to produce a reduced complexity sample. The invention further provides for analysis of the above sample to interrogate sequences of interest such as polymorphisms. The amplified sample may be hybridized to an array, which may be specifically designed to interrogate the desired fragments for the presence or absence of a polymorphism.

27 Claims, 8 Drawing Sheets

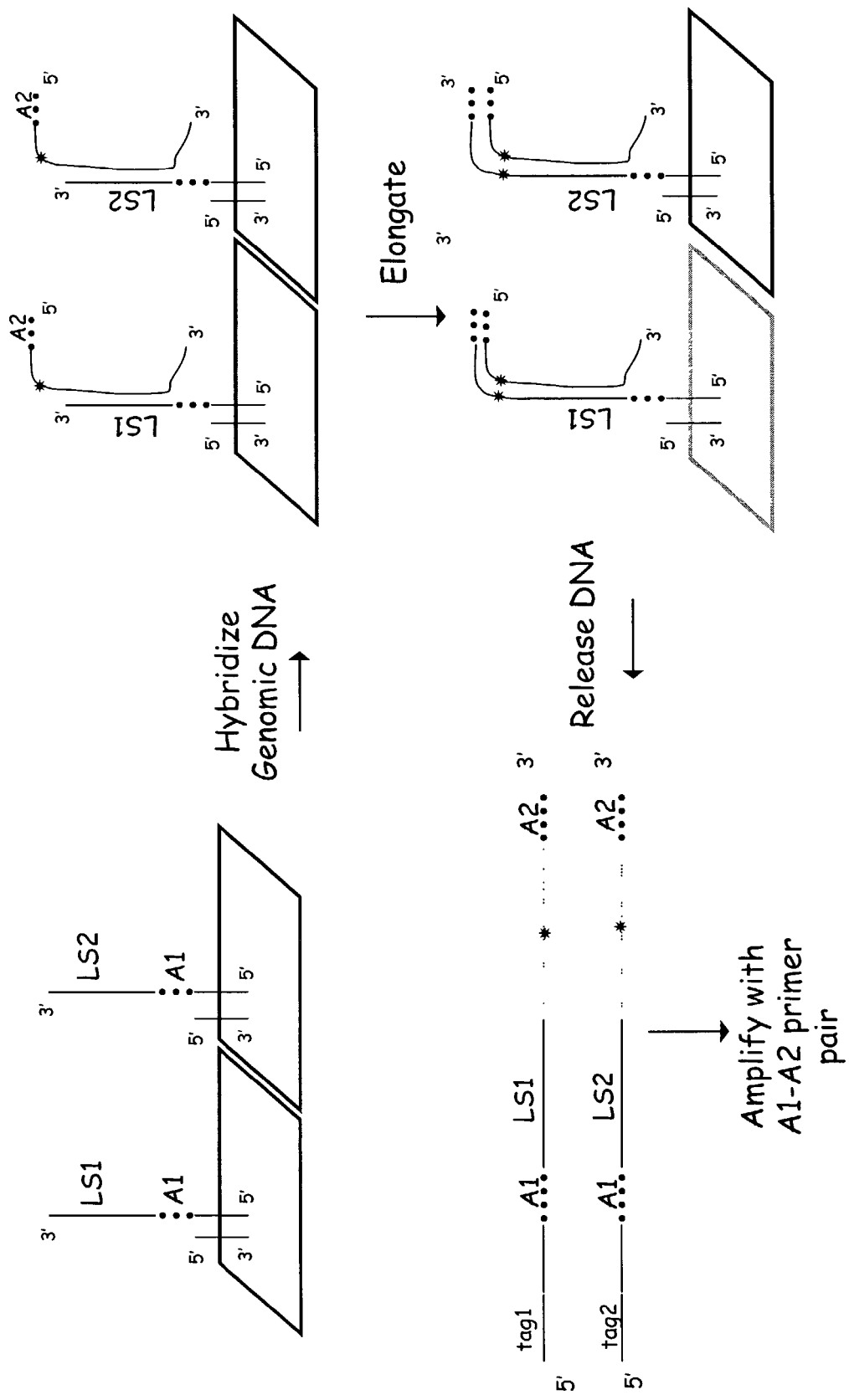

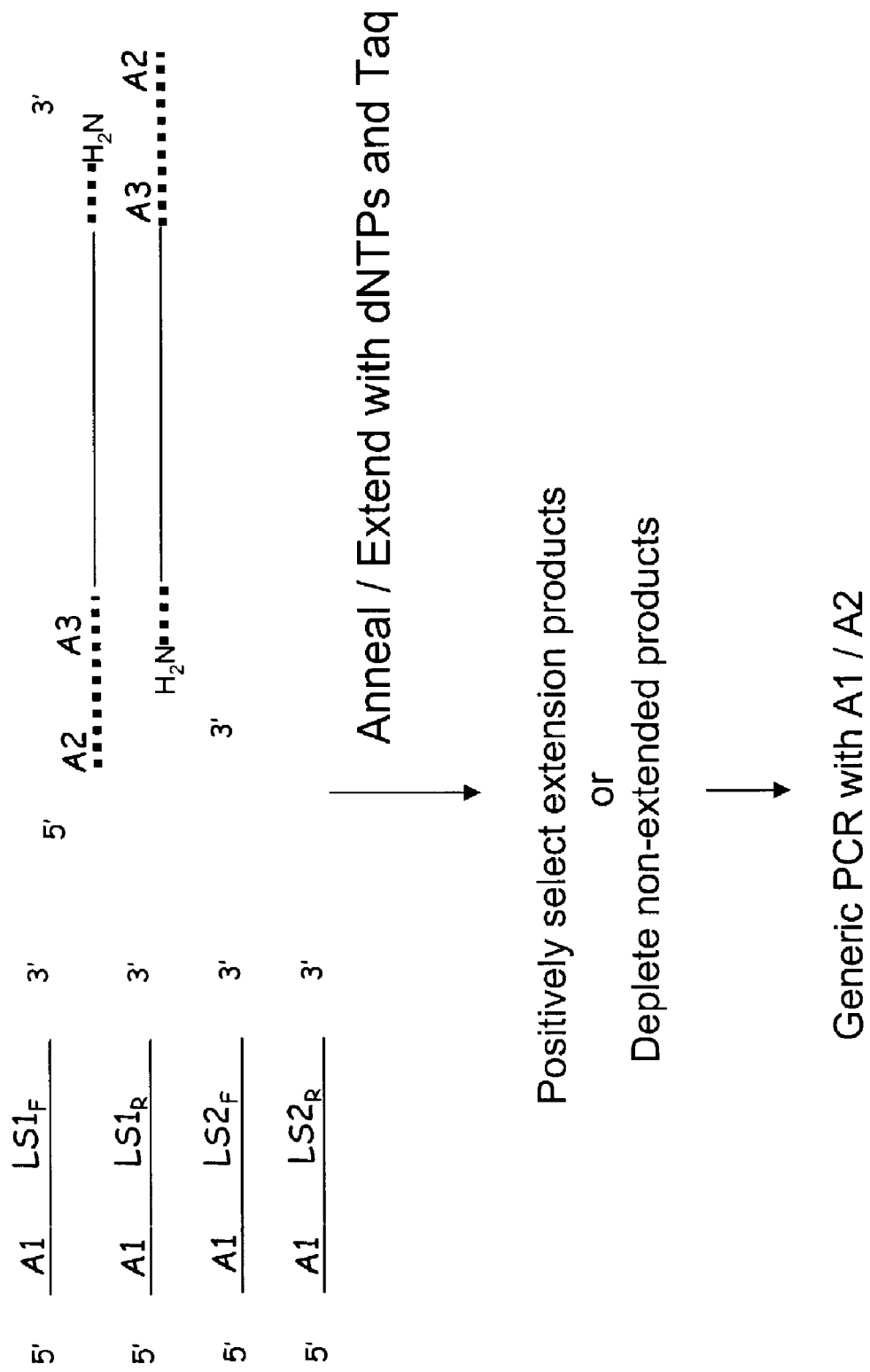

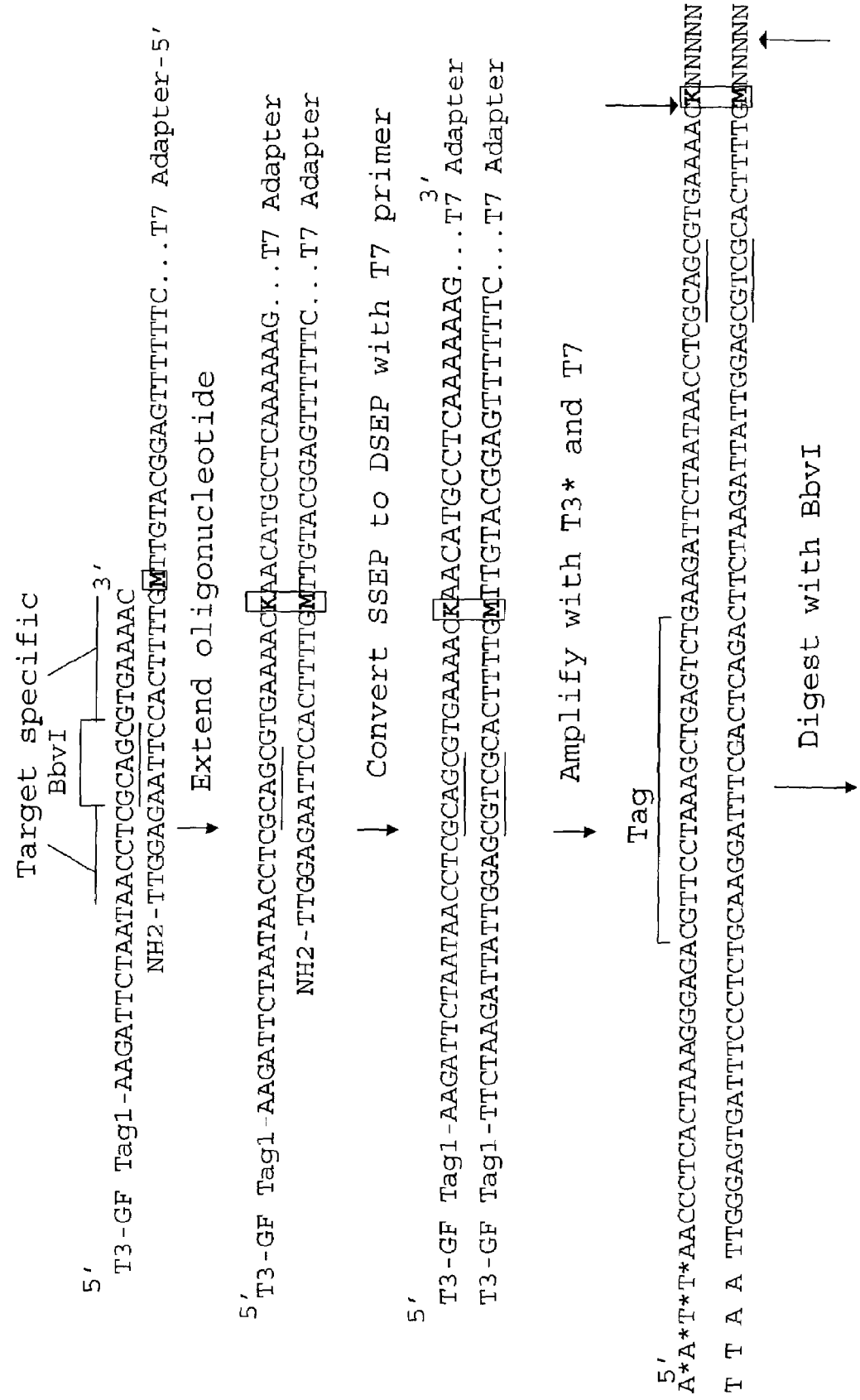

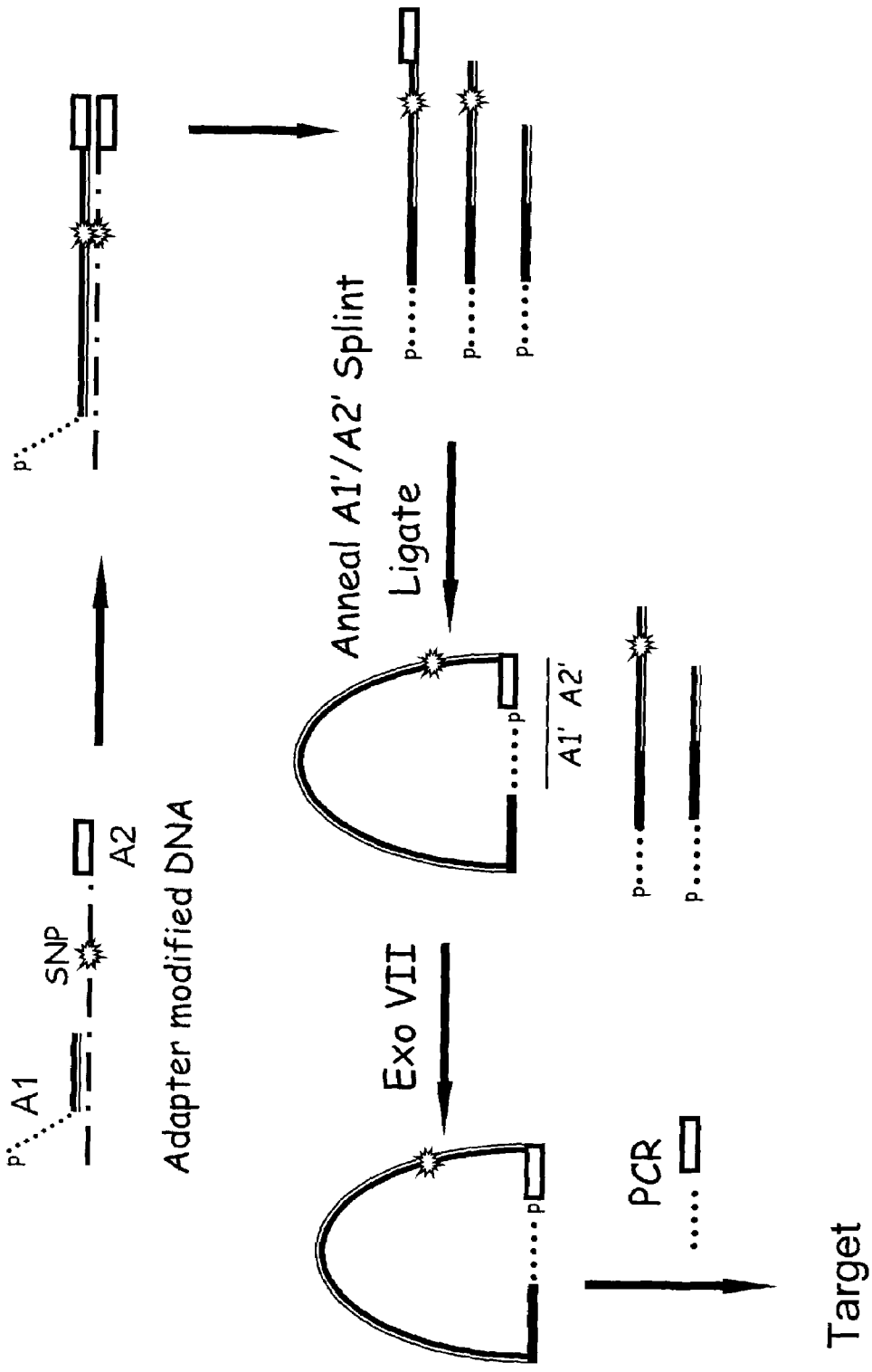

COMPLEXITY MANAGEMENT OF GENOMIC DNA BY LOCUS SPECIFIC AMPLIFICATION

FIELD OF THE INVENTION

The invention relates to enrichment and amplification of a collection of target sequences from a nucleic acid sample and methods of analyzing amplified product. In some embodiments target sequences are amplified by extension of a locus-specific primer followed by amplification of the extended locus-specific primer with a generic pair of primers. In some embodiments the locus-specific primers are attached to a solid support and extension takes place on the solid support. In some embodiments the invention relates to the preparation of target for array based analysis of genotype. The present invention relates to the fields of molecular biology and genetics.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

Single nucleotide polymorphisms (SNPs) have emerged as the marker of choice for genome wide association studies and genetic linkage studies. Building SNP maps of the genome will provide the framework for new studies to identify the underlying genetic basis of complex diseases such as cancer, mental illness and diabetes. Due to the wide ranging applications of SNPs there is still a need for the development of robust, flexible, cost-effective technology platforms that allow for scoring genotypes in large numbers of samples.

SUMMARY OF THE INVENTION

The present invention provides for novel methods of sample preparation and analysis comprising managing or reducing the complexity of a nucleic acid sample by amplification of a collection of target sequences using target specific capture probes. In some embodiments the extended capture probes are attached to a solid support; in some embodiments the extended capture probes are in solution. In some embodiments the amplified collection of target sequences is analyzed by hybridization to an array that is designed to interrogate sequence variation in the target sequences. In some embodiments the amplified collection of target sequences is analyzed by hybridization to an array of tag probes.

In one embodiment a method of amplifying a collection of target sequences from a nucleic acid sample is disclosed. A collection of capture probes is generated. The collection comprised a plurality of different species of primers wherein each species comprises a first common sequence and a 3' variable region that is specific for a target sequence in the collection of target sequences. Each target sequence is represented by at least one species of primer which hybridizes to the target sequence and the collection of capture probes is attached to a solid support so that the 3' end of the capture probes is available for extension. The nucleic acid sample is fragmented and an adapter that has a second common sequence is ligated to the fragments. Fragmentation in some embodiments is by one or more restriction enzymes. The adapter-ligated fragments are hybridized to the collection of capture probes and the capture probes are extended using the hybridized adapter-ligated fragments as template for extension and thereby incorporating the target sequence and the second common sequence into the 3' end of the extended capture probe. The extended capture probes are then amplified using first and second common sequence primers.

In some embodiments the capture probes are attached to the solid support through a covalent interaction. In another embodiment there is a tag sequence in the capture probes that is unique for each species of capture probe and the capture probes are attached to the solid support by hybridization to a collection of tag probes that are covalently attached to the solid support. In some embodiments each species of capture probe is attached to the solid support in a discrete location.

In another embodiment the extended capture probes are released from the solid support prior to amplification. Prior to releasing the extended capture probes from the solid support nucleic acids that are not covalently attached to the solid support may be removed.

In another embodiment the extended capture probes are enriched prior to amplification. In some embodiments capture probes are enriched by incorporation of labeled nucleotides into the extended capture probes followed by isolation of labeled capture probes by affinity chromatography. In some embodiments capture probes are labeled with biotin and avidin, streptavidin or an anti-biotin antibody, which may be monoclonal, may be used to isolate extended capture probes. In another embodiment extended capture probes are made double stranded and single stranded nucleic acid in the sample is digested by, for example a nuclease, such as, for example Exonuclease I. In another embodiment the extended capture probes are circularized prior to amplification and uncircularized nucleic acid in the sample is digested by, for example, a nuclease, such as, for example, Exonuclease III. In some embodiments the extended capture probes are circularized by hybridizing an oligonucleotide splint to the extended capture probes so that the 5' and 3' ends of extended capture probes are juxtaposed and then ligating the ends of the extended capture probes.

In one embodiment a method of genotyping one or more polymorphic locations in a sample is disclosed. An amplified collection of target sequences from the sample is prepared and hybridized to an array designed to interrogate at least one polymorphic location in the collection of target sequences. The hybridization pattern is analyzed to determine the identity of the allele or alleles present at one or more polymorphic location in the collection of target sequences.

In another embodiment a method for analyzing sequence variations in a population of individuals is disclosed. A nucleic acid sample is obtained from each individual and a collection of target sequences from each nucleic acid sample is amplified. Each amplified collection of target sequences is hybridized to an array designed to interrogate sequence variation in the collection of target sequences to generate a hybridization pattern for each sample and the hybridization patterns are analyzed or compared to determine the presence or absence of sequence variation in the population of individuals.

In another embodiment a method of amplifying a collection of target sequences from a nucleic acid sample in solution is disclosed. A collection of capture probes is generated. The collection comprised a plurality of different species of primers wherein each species comprises a first common sequence and a 3' variable region that is specific for a target sequence wherein each target sequence in a collection of target sequences is represented by at least one species of primer which hybridizes to the target sequence. The nucleic acid sample is fragmented and an adapter is ligated to the fragments so that the strand that is ligated to the 5' end of the fragment strands comprises a second common sequence and the strand that is ligated to the 3' end of the fragments lacks the second common sequence and is blocked from extension at the 3' end. The adapter-ligated fragments are hybridized to the collection of capture probes and the capture probes are extended using the hybridized adapter-ligated fragments as template for extension and thereby incorporating the target sequence and the complement of the second common sequence into the extended capture probes. The extended capture probes are then amplified with first and second common sequence primers.

In one embodiment an amino group is used to block extension at the 3' end of the adapter strand.

In some embodiments fragmentation of the nucleic acid sample is by digestion with one or more restriction enzymes.

In another embodiment a method for genotyping one or more polymorphisms in a nucleic acid sample is disclosed. The nucleic acid sample is fragmented and an adapter comprising a first common priming sequence is ligated to the fragments. A collection of capture probes is ligated to the fragments. The capture probes have a second common priming sequence, a tag sequence unique for each species of capture probe, a first locus specific sequence, a Type IIs restriction enzyme recognition sequence, and a second locus specific sequence. The Type IIs restriction enzyme recognition sequence is positioned so that the enzyme will cut immediately 5' of the polymorphic base in a target sequence. The capture probes are extended to generate single-stranded extension products and then amplified using the first and second common sequence primers. The the amplified product is digested with a Type IIs restriction enzyme and the fragments are extended in the presence of one or more type of labeled ddNTP. In one embodiment the extension is done is four separate reactions, one for each ddNTP and the ddNTPs may be labeled with the same label. The extended fragments are then hybridized to four separate arrays. In another embodiment the ddNTPs are differentially labeled with at least two different labels and the extension reactions may be done in less than four reactions and each reaction may be hybridized to a separate array. The arrays are arrays of tag probes tat hybridize to the tag sequences in the capture probes. The hybridization pattern on each of the arrays is analyzed to determine at least one genotype.

In some embodiments the ddNTPs are labeled with biotin.

In another embodiment one of the common sequence primers is resistant to nuclease digestion and the sample is treated with a nuclease that cleaves 5' to 3' after the fragments are extended in the presence of labeled ddNTP. In one embodiment the primer is resistant to nuclease digestion because it contains phosphorothioate linkages. In some embodiments the nuclease is T7 Gene 6 Exonuclease.

In another embodiment a method for screening for sequence variations in a population of individuals is disclosed. A nucleic acid sample from each individual is provided and the sample is amplified and genotyped by one of the method of the invention and the genotypes from the samples are compared to determine the presence or absence of sequence variation in the population of individuals.

In another embodiment a kit for amplifying a collection of target sequences is disclosed. The kit has a collection of capture probes that is specific for a collection of target sequences and has a first common sequence that is common to all of the capture probes, an adapter that has a second common sequence; and a pair of first and second common sequence primers. In another embodiment the collection of capture probes in the kit is covalently attached to a solid support so that the 3' end of the capture probes is available for extension. In another embodiment the kit also provides a restriction enzyme, buffer, DNA polymerase and dNTPs. In some embodiments the restriction enzyme is a Type IIs restriction enzyme. In another embodiment the kit also contains a ligase, dNTPs, ddNTPs, buffer and DNA polymerase. In some embodiments one of the common sequence primers is resistant to nuclease digestion.

In another embodiment the capture probes also have a tag sequence unique for each species of capture probe and a Type IIs restriction enzyme recognition sequence. In another embodiment the adapter has a first strand comprising a common sequence and a second strand that does not contain the complement of that common sequence and the second strand is blocked from extension at the 3' end by, for example, an amino group.

In another embodiment a collection of capture probes attached to a solid support is disclosed. The solid support may be arrays, beads, microparticles, microtitre dishes or gels.

In another embodiment a plurality of oligonucleotides attached to a solid support is disclosed. The solid support may be arrays, beads, microparticles, microtitre dishes or gels. The oligonucleotides may be released and used for a variety of analysis. The plurality of oligonucleotides may comprise a collection of capture probes.

BRIEF DESCRIPTION OF THE FIGURES

FIG. 2 shows a method where the capture probes are attached to a solid support by hybridization to a probe that is covalently attached to the solid support. The probes on the array are complementary to a tag sequence in the 5' region of the capture probe. The capture probe hybridizes so that the 3' end is available for extension.

FIG. 3 shows a schematic of solution-based multiplexed SNP genotyping. A sample is fragmented and ligated to an adapter so that the adapter sequence that hybridizes to the 3' end of the strands of the fragments is blocked from extension. Locus specific capture probes are hybridized to the fragments and extended in solution then amplified by PCR using primers to A1 and A2. Prior to amplification the extended capture probes may be enriched by, for example, removal of non-extended products or by positive selection of extended products.

FIG. 7 shows another enrichment scheme. The ends of the extended capture probes are ligated together to form a circle using a splint oligonucleotide that is complementary to the primer sites at the ends of the extended capture probes. The sample is digested with an exonuclease so circularized sequences are protected from digestion.

Figure 1:
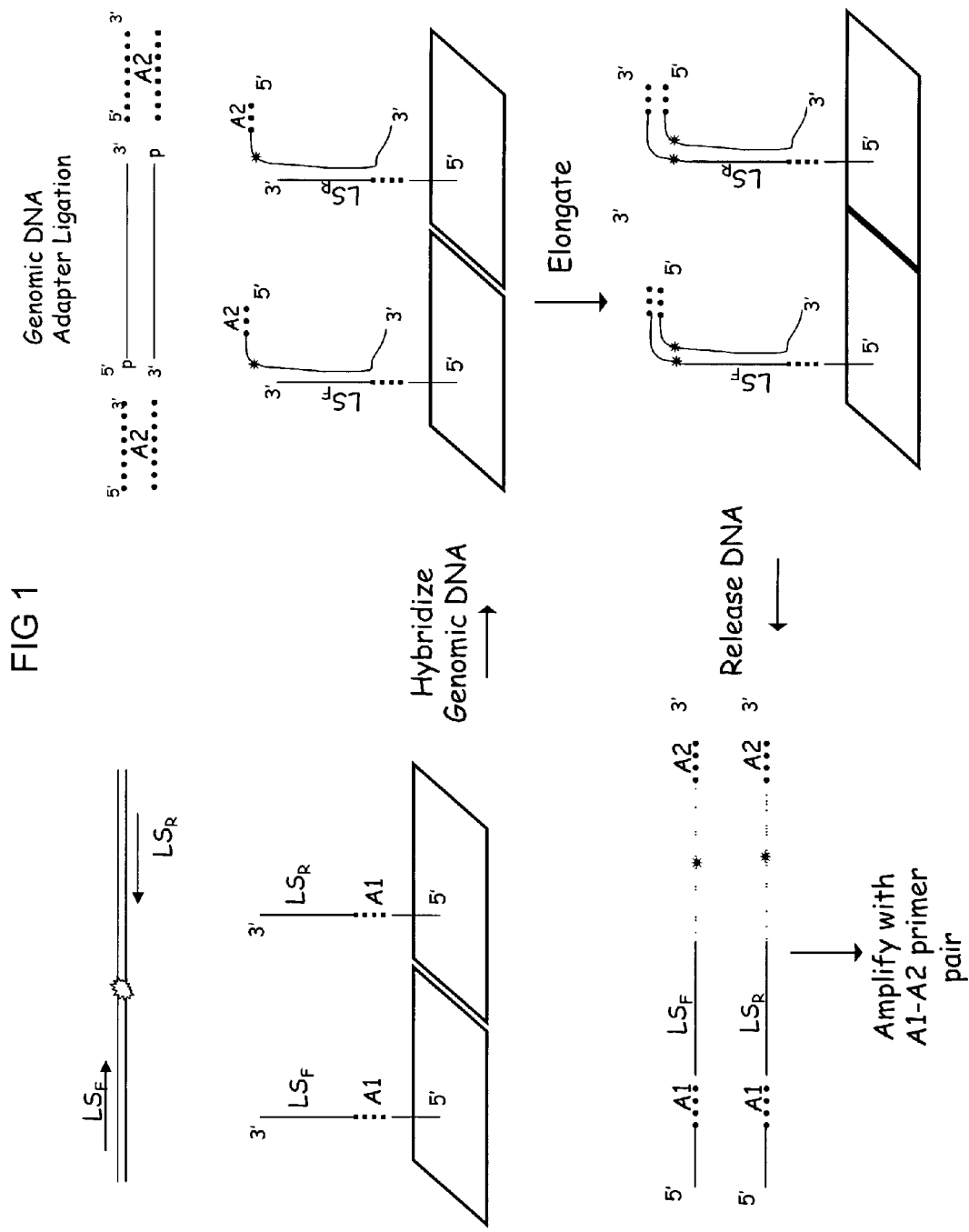
FIG. 1 shows a method of amplifying specific target sequences using a capture probe that is locus specific and genomic DNA that has been ligated to an adapter. The capture probes are attached to a solid support and extended to incorporate the sequence of interest and the adapter sequence. The extended capture probes are released from the solid support and amplified with a single primer pair.

DETAILED DESCRIPTION OF THE PREFERRED EMBODIMENTS (A) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, 10, $10^{-1}$, $10^{-2}$, $10^{-3}$, $10^{-4}$, or $10^{-5}$, for example. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer (anyone have the cite), Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y. all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,136,269, in PCT Applications Nos. PCT/US99/00730 (International Publication Number WO 99/36760) and PCT/US 01/04285, and in U.S. patent application Ser. Nos. 09/501,099 and 09/122,216 which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165 and 5,959,098 which are each incorporated herein by reference in their entirety for all purposes. Nucleic acid arrays are described in many of the above patents, but the same techniques are applied to polypeptide arrays.

The present invention also contemplates many uses for polymers attached to solid substrates. These uses include gene expression monitoring, profiling, library screening, genotyping, and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. No. 10/013,598, and U.S. Pat. Nos. 5,856,092, 6,300,063, 5,858,659, 6,284,460, 6,361,947, 6,368,799 and 6,333,179 which are each incorporated herein by reference. Other uses are embodied in U.S. Pat. Nos. 5,871,928, 5,902,723, 6,045,996, 5,541,061, and 6,197,506 which are incorporated herein by reference.

The present invention also contemplates sample preparation methods in certain preferred embodiments. For example, see the patents in the gene expression, profiling, genotyping and other use patents above, as well as U.S. Ser. No. 09/854,317, U.S. Pat. Nos. 5,437,990, 5,215,899, 5,466,586, 4,357,421, and Gubler et al., 1985, Biochemica et Biophysica Acta, Displacement Synthesis of Globin Complementary DNA: Evidence for Sequence Amplification.

Prior to or concurrent with analysis, the nucleic acid sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990), WO/88/10315 and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/512,300, 09/916,135, 09/920,491, 09/910,292, and 10/013,598, which are incorporated herein by reference in their entireties.

The present invention also contemplates detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over the internet. See U.S. patent applications and provisional application Ser. No. 10/063,559, Nos. 60/349,546, 60/376,003, 60/394,574, and 60/403,381

The present invention provides a flexible and scalable method for analyzing complex samples of nucleic acids, such as genomic DNA. These methods are not limited to any particular type of nucleic acid sample: plant, bacterial, animal (including human) total genome DNA, RNA, cDNA and the like may be analyzed using some or all of the methods disclosed in this invention. The word "DNA" may be used below as an example of a nucleic acid. It is understood that this term includes all nucleic acids, such as DNA and RNA, unless a use below requires a specific type of nucleic acid. This invention provides a powerful tool for analysis of complex nucleic acid samples. From experimental design to isolation of desired fragments and hybridization to an appropriate array, the invention provides for fast, efficient and inexpensive methods of complex nucleic acid analysis.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793–800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations (see, for example, U.S. Ser. No. 09/358,664). Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3$^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4_6$) base pairs while a four base pair recognition sequence will occur once every 256 ($4_4$) base pairs. In silico digestions of sequences from the Human Genome Project show that the actual occurrences may be more or less frequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes see, New England BioLabs Catalog which is herein incorporated by reference in its entirety for all purposes).

Type-IIs endonucleases are a class of endonuclease that, like other endonucleases, recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end." The Type-IIs endonucleases are unique because they generally do not require palindromic recognition sequences and they generally cleave outside of their recognition sites. For example, the Type-I's endonuclease EarI recognizes and cleaves in the following manner:

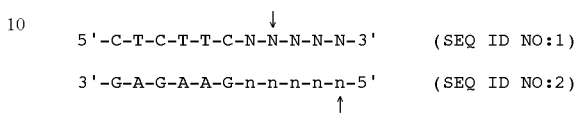

where the recognition sequence is -C-T-C-T-T-C-, N and n represent complementary, ambiguous base pairs and the arrows indicate the cleavage sites in each strand. As the example illustrates, the recognition sequence is non-palindromic, and the cleavage occurs outside of that recognition site.

Type-IIs endonucleases are generally commercially available and are well known in the art. Specific Type-IIs endonucleases which are useful in the present invention include, e.g., BbvI, BceAI, BfuAI, EarI, AlwI, BbsI, BsaI, BsmAI, BsmBI, BspMI, HgaI, SapI, SfaNI, BsmFI, FokI, and PleI. Other Type-IIs endonucleases that may be useful in the present invention may be found, for example, in the New England Biolabs catalogue. In some embodiments Type-IIs enzymes that generate a recessed 3' end are particularly useful.

"Adapter sequences" or "adapters" are generally oligonucleotides of at least 5, 10, or 15 bases and preferably no more than 50 or 60 bases in length; however, they may be even longer, up to 100 or 200 bases. Adapter sequences may be synthesized using any methods known to those of skill in the art. For the purposes of this invention they may, as options, comprise primer binding sites, recognition sites for endonucleases, common sequences and promoters. The adapter may be entirely or substantially double stranded. A double stranded adapter may comprise two oligonucleotides that are at least partially complementary. The adapter may be phosphoxylated or unphosphorylated on one or both strands. Adapters may be more efficiently ligated to fragments if they comprise a substantially double stranded region and a short single stranded region which is complementary to the single stranded region created by digestion with a restriction enzyme. For example, when DNA is digested with the restriction enzyme EcoRI the resulting double stranded fragments are flanked at either end byte single stranded overhang 5'-AATT-3', an adapter that carries a single stranded overhang 5'-AATT-3' will hybridize to the fragment through complementarity between the overhanging regions. This "sticky end" hybridization of the adapter to the fragment may facilitate ligation of the adapter to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be convened to blunt ends by filling in an overhang or removing an overhang.

Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art.

When a fragment has been digested on both ends with the same enzyme or two enzymes that leave the same overhang, the same adapter may be ligated to both ends. Digestion with two or more enzymes can be used to selectively ligate separate adapters to either end of a restriction fragment. For example, if a fragment is the result of digestion with EcoRI at one end and BantHI at the other end, the overhangs will be 5'-AATT-3' and 5'GATC-3', respectively. An adapter with an overhang of AATT will be preferentially ligated to one end while an adapter with an overhang of GATC will be preferentially ligated to the second end.

Au adapter may be ligated to one or both strands of the fragmented DNA. In some embodiments a double stranded adapter is used but only one strand is ligated to the fragments. Ligation of one strand of an adapter may be selectively blocked. Any known method to block ligation of one strand may be employed. For example, one strand of the adapter can be designed to introduce a gap of one or more nucleotides between the 5' end of that strand of the adapter and the 3' end of the target nucleic acid. Adapters can be designed specifically to be ligated to the termini produced by restriction enzymes and to introduce gaps or nicks. For example, if the target is an EcoRI digested fragment an adapter with a 5' overhang of TTA could be ligated to the AATT overhang left by EcoRI to introduce a single nucleotide gap between the adapter and the 3' end of the fragment. Phosphorylation and kinasing can also be used to selectively block ligation of the adapter to the 3' end of the target molecule. Absence of a phosphate from the 5' end of an adapter will block ligation of that 5' end to an available 3'OH. For additional adapter methods for selectively blocking ligation see U.S. Pat. No. 6,197,557 and U.S. Ser. No. 09/910,292 which are incorporated by reference herein in their entirety for all purposes.

adapters may also incorporate modified nucleotides that modify the properties of the adapter sequence. For example, phosphorothioate groups may be incorporated in one of the adapter strands. A phosphorothioate group is a modified phosphate group with one of the oxygen atoms replaced by a sulfur atom. In a phosphorothioated oligo (often called an "S-Oligo"), some or all of the internucleotide phosphate groups are replaced by phosphorothioate groups. The modified backbone of an S-Oligo is resistant to the action of most exonucleases and endonucleases. Phosphorothioates may be incorporated between all residues of an adapter strand, or at specified locations within a sequence. A useful option is to sulfurize only the last few residues at each end of the oligo. This results in an oligo that is resistant to exonucleases, but has a natural DNA center.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000, 000 bp. For example, the size of the entire human genome is about $3\times10^9$ bp. The largest chromosome, chromosome no. 1, contains about $2.4\times10^8$ bp while the smallest chromosome, chromosome no. 22, contains about $5.3\times10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, insertion elements such as Alu or small insertions or deletions, for example, deletions or insertions of 1–10 bases. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. When an organism carries two identical alleles the organism is homozygous at that position. When an organism carries two different alleles the organism is heterozygous at that position. Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

Single nucleotide polymorphisms (SNPs) are positions at which two alternative bases occur at appreciable frequency (>1%) in the human population, and are the most common type of human genetic variation. The site is usually preceded by and followed by highly conserved sequences of the allele (e.g., sequences that vary in less than $\frac{1}{100}$ or $\frac{1}{1000}$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A diallelic polymorphism has two forms in a population. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Capture probes are oligonucleotides that have a 5' common sequence and a 3' locus or target specific region or primer. The locus or target specific region is designed to hybridize near a region of nucleic acid that includes a region of interest so that the locus or target specific region of the capture probe can be used as a primer and be extended through the region of interest to make a copy of the region of interest. The common sequence in the capture probe may be used as a priming site in subsequent rounds of amplification using a common primer or a limited number of common primers. The same common sequence may be present in many or all or the capture probes in a collection of capture probes. Capture probes may also comprise other sequences, for example, tag sequences that are unique for different species of capture probes, and endonuclease recognition sites.

A tag or tag sequence is a selected nucleic acid with a specified nucleic acid sequence. A tag probe has a region that is complementary to a selected tag. A set of tags or a collection of tags is a collection of specified nucleic acids that may be of similar length and similar hybridization properties, for example similar $T_m$. The tags in a collection of tags bind to tag probes with minimal cross hybridization so that a single species of tag in the tag set accounts for the majority of tags which bind to a given tag probe species under hybridization conditions. For additional description of tags and tag probes and methods of selecting tags and tag probes see U.S. Ser. No. 08/626,285 and EP/0799897, each of which is incorporated herein by reference in their entirety.

A collection of capture probes may be designed to interrogate a collection of target sequences. The collection would comprise at least one capture probe for each target sequence to be amplified. There may be multiple different capture probes for a single target sequence in a collection of capture probes, for example, there may be a capture probe that hybridizes to one strand of the target sequence and a capture probe that hybridizes to the opposite strand of the target sequence, these may be referred to as a forward locus or target specific primer and a reverse locus or target specific primer. There also may be two or more capture probes that hybridize at different locations downstream of the target sequence.

A collection of capture probes may be used to amplify a subset of a genome. The collection of capture probes may be initially used to generate a copy of the target sequences in the genomic sample and then the copies may be amplified using common primers. The amplification may be done simultaneously in the same reaction and often in the same tube.

The term "target sequence", "target nucleic acid" or "target" refers to a nucleic acid of interest. The target sequence may or may not be of biological significance. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, and DNA encoding or believed to encode regulatory regions such as promoter sequences, splicing signals, polyadenylation signals, etc. The number of sequences to be interrogated can vary, but preferably are from about 1000, 2,000, 5,000, 10,000, 20,000 or 100,000 to 5000, 10,000, 100,000, 1,000,000 or 3,000,000 target sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science*, 251:767–777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix under the brand name GeneChip® and are directed to a variety of purposes, including genotyping and gene expression monitoring for a variety of eukaryotic and prokaryotic species. (See Affymetrix Inc., Santa Clara and their website at affymetrix.com.)

Hybridization probes are oligonucleotides capable of binding in a base-specific manner to a complementary strand of nucleic acid. Such probes include peptide nucleic acids, as described in Nielsen et al., *Science* 254, 1497–1500 (1991), and other nucleic acid analogs and nucleic acid mimetics. See U.S. patent application Ser. No. 08/630,427-filed Apr. 3, 1996.

The term "hybridization" refers to the process in which two single-stranded polynucleotides bind non-covalently to form a double-stranded polynucleotide; triple-stranded hybridization is also theoretically possible. The resulting double-stranded polynucleotide is a "hybrid." The hybrid may have double-stranded regions and single stranded regions.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see, for example, Sambrook et al., (2001) which is hereby incorporated by reference in its entirety for all purposes above.

An individual is not limited to a human being, but may also include other organisms including but not limited to mammals, plants, bacteria or cells derived from any of the above.

(C.) Multiplexed Anchored Runoff Amplification

Generally, the invention provides methods for highly multiplexed locus specific amplification of nucleic acids and methods for analysis of the amplified products. In some embodiments the invention combines the use of capture probes that comprise a common sequence and a locus-specific region with adapter-modified sample nucleic acid; the adapter comprises a second common sequence. The capture probes are extended to produce copies of the sample DNA that contain common priming sequences flanking the target sequence. The copies are amplified with a generic set of primers that recognize the common sequences. The amplified product may be analyzed by hybridization to an array of probes.

In one embodiment the steps of the invention comprise: generating capture probes; digesting a nucleic acid sample; ligating adapters to the fragmented sample; mixing the fragments and the capture probes under conditions that will allow hybridization of the fragments and the capture probes; extending the capture probes in the presence of dNTPs and polymerase; amplifying the extended capture probes; and detecting the presence or absence of target sequences of interest.

One embodiment of the methods is illustrated in FIG. 1. Capture probes are designed with a locus specific region ($LS1_F$ and $LS1_R$) that hybridizes near a target sequence of interest and a common sequence (A1) that is 5' of the locus specific region. The common priming site may be present in a plurality of capture probes so that a primer to A1 may be used for amplification of a plurality of different targets in subsequent steps. The capture probes are attached to a solid support so that they have a free 3' end. A plurality of a single species of capture probes may be synthesized at a discreet location on an array and may form a discrete feature of an array. Each feature of the array may contain a different species of locus specific capture probe.

Genomic DNA is fragmented and adapters comprising a second common sequence (A2) are ligated to the fragments. The adapter-ligated fragments are then mixed with the capture probes under conditions that allow hybridization of the fragments to the capture probes on the array. The capture probes are then extended using the adapter-ligated fragments as template. The extension product has a common sequence, A1, near its 5' end and a second common sequence A2 near its 3' end. These common sequences flank a region of interest. The capture probes are then released from the array and extended capture probes are amplified by PCR using primers to the common sequences A1 and A2. The amplified product may then be analyzed by, for example, hybridization to an array. Information about the region of interest can be determined by analysis of the hybridization pattern.

A second embodiment of the methods is illustrated in FIG. 2. Capture probes are designed with a locus specific region (LS1 or LS2) and a common sequence (A1) as in FIG. 1. In this embodiment the capture probes further comprise a tag sequence that is unique for each species of capture probe designed. (For a description of tags and tag probes, see, U.S. Ser. No. 08/626,285.) The capture probes are attached to the array through hybridization of the tag sequence to a substantially complementary tag probe sequence that is attached to the array. The tag probes may be attached to the array in discrete locations. Different species of tag probes are present at different discrete, spatially addressable locations. Adapter-ligated genomic DNA is hybridized to the array so that the capture probes hybridize to target sequences in the sample. The capture probes are extended as in FIG. 1 to incorporate the target sequence and common sequence A2. The extended capture probes are released and amplified using primers A1 and A2. The amplified product may then be analyzed by, for example, hybridization to an array. Information about the region of interest can be determined by analysis of the hybridization pattern. The amplified sample may be analyzed by any method known in the art, for example, MALDI-TOF mass spec, capillary electrophoresis, OLA, dynamic allele specific hybridization (DASH) or TaqMan® (Applied Biosystems, Foster City, Calif.). For other methods of genotyping analyses see Syvanen, *Nature Rev. Gen.* 2:930–942 (2001) which is herein incorporated by reference in its entirety.

In some embodiments the capture probes are attached to a solid support prior to hybridization and hybridization takes place while the capture probes are attached to the solid support. In some embodiments the capture probes are synthesized on a solid support. Any suitable solid support known in the art may be used, for example, arrays, beads, microparticles, microtitre dishes and gels may be used. In some embodiments the capture probes are synthesized on an array in a 5' to 3' direction.

In some embodiments hybridization and extension of capture probes are done while the capture probes are attached to a solid support. Following extension of the capture probes nucleic acids that are not covalently attached to the solid support may be washed away. In some embodiments the extended capture probes are released from the solid support prior to amplification. In another embodiment amplification takes place while the extended capture probes are attached to the solid support. The extended capture probes may be released from the solid support by, for example, using a reversible linker or an enzymatic release, such as an endonuclease or by a change in conditions that results in disruption of an interaction between the capture probe and the solid support, for example, when capture probes are associated with the solid support through base pairing between a tag in the capture probe and a tag probe on the solid support, disruption of the base pairing interaction releases the capture probes from the solid support. Enzymatic methods include, for example, use of uracil DNA glycosylase (UDG) or (UNG). UNG catalyzes the hydrolysis of DNA that contains deoxyuridine at the site the uridine is incorporated. Incorporation of one or more uridines in the capture probe followed by treatment with UNG will result in release of the capture probe from the solid support. A thermolabile UNG may also be used In some embodiments a collection of target sequences is analyzed. A plurality of capture probes is designed for a plurality of target sequences. In some embodiments target sequences contain or are predicted to contain a polymorphism, for example, a SNP. The polymorphism may be, for example, near a gene that is a candidate marker for a phenotype, useful for diagnosis or a disorder or for carrier screening or the polymorphism may define a haplotype block (see, Daly et al. *Nat Genet.* 29:229–32 (2001), and Rioux et al. *Nat Genet.* 29:223–8 (2001) and U.S. patent application Ser. No. 10/213,272, each of which is incorporated herein by reference in its entirety). A collection of capture probes may be designed so that capture probes hybridize near a polymorphism, for example, within 1, 5, 10, or 100 to 5, 10, 100, 1000, 10,000 or 100,000 bases from the polymorphism. The capture probes hybridize to one strand of the target sequence and can be extended through the polymorphic site or region so that the extension product comprises a copy of the polymorphic region.

Many amplification methods are most efficient at amplification of smaller fragments. For example, PCR most efficiently amplifies fragments that are smaller than 2 kb (see, Saiki et al. 1988). In one embodiment capture probes and fragmentation conditions are selected for efficient amplification of a selected collection of target sequences. The size of the amplified fragments is dependent on where the target specific region of the capture probe hybridizes to the target sequence and the 5' end of the fragment strand that the capture probe is hybridized to. In some embodiments of the present methods capture probes and fragmentation methods are designed so that the target sequence of interest can be amplified as a fragment that is, for example, less than 20,000, 2,000, 800, 500, 400, 200 or 100 base pairs long. The capture probe can be designed so that the 3' end of the target specific region hybridizes to the base that is just 3' of a position to be interrogated in the target sequence. For example, if the sequence to be interrogated is a polymorphism and the sequence is 5'-GCTXATCGG-3', where X is the polymorphic position, the target specific region of the capture probe may have the sequence 5'-CCGAT-3'. When the sample is fragmented with site specific restriction enzymes the length of the fragments will also depend on the position of the nearest recognition site for the enzyme or enzymes used for fragmentation. A collection of target sequences may be selected based on proximity to restriction sites. In some embodiments target sequences are selected for amplification and analysis based on the presence of a sequence of interest, such as a SNP, and proximity to a cleavage site for a selected restriction enzyme. For example, SNPs that are within 200, 500, 800, 1,000, 1,500, 2,000 or 20,000 base pairs of either a restriction site, such as, for example, an EcoRI site, a BglI site, an XbaI site or any other restriction enzyme site may be selected to be target sequences in a collection of target sequences. In another method a fragmentation method that randomly cleaves the sample into fragments that are 30,100, 200, 500 or 1,000 to 100, 200, 500, 1,000 or 2,500 base pairs on average may be used.

In another embodiment, illustrated in FIG. 3, the capture probes are in solution and hybridization and extension take place in solution. In this embodiment the nucleic acid sample is fragmented and adapter containing common sequences A2 and A3 is ligated to the fragments. In some embodiments one strand of the adapter, the strand that is ligated to the 3' end of the fragment strands lacks common sequence A2 and is blocked from extension at the 3' end. Ligation of the blocked adapter strand to the 3' end of the fragment strands prevents the fragments from being extended to incorporate A2 at both ends, thus preventing amplification of the fragments by primer A2 in the subsequent PCR amplification step. Capture probes with locus specific regions and common sequence A1 are mixed with the adapter-ligated fragments under conditions that allow hybridization of the capture probes to the adapter ligated fragments. The capture probes are extended in the presence of polymerase and dNTPs. In some embodiments the extended capture probes are positively selected to generate a sample that is enriched for extended capture probes. In another embodiment extended capture probes are enriched by depleting non-extended products.

Figure 4B:
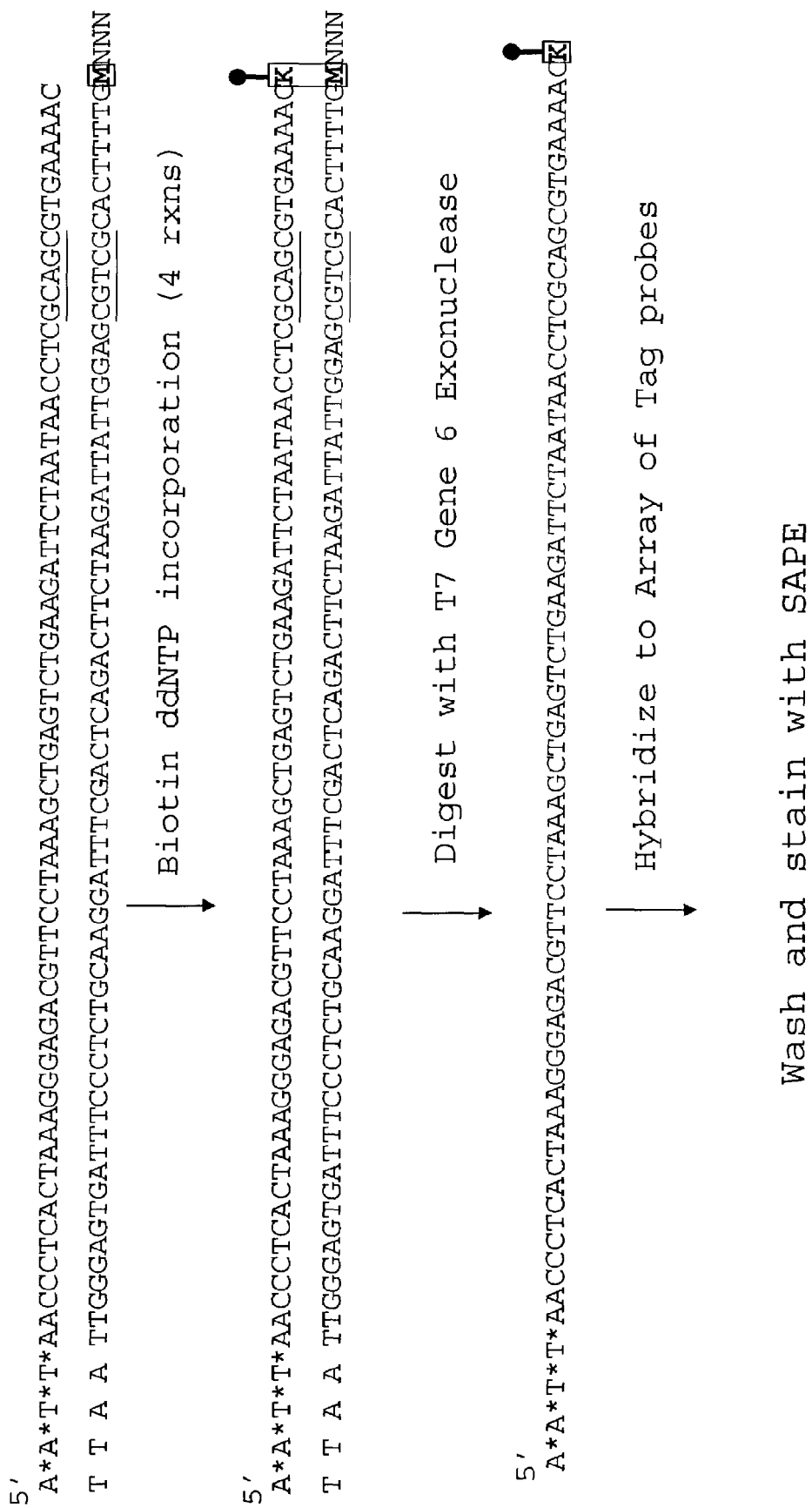
FIG. 4 shows a method of multiplexed anchored runoff amplification wherein the alleles present at different polymorphic positions are analyzed by hybridization to an array of tag probes. The capture probe includes a recognition site for a Type IIs restriction enzyme so that the enzyme cuts immediately upstream of the polymorphic locus. The capture probe is extended by one labeled nucleotide and the identity of the nucleotide is determined by hybridization to an array or probes that are complementary to the tag sequences in the capture probes.

In another embodiment the capture probes comprise a first common sequence, a tag sequence, a target sequences and a recognition sequence for a Type IIs restriction enzyme (see, FIGS. 4a and 4b, SEQ ID NOS: 4–12). The Type IIs recognition site is inserted within the target specific region so that there is target specific sequence on either side of the Type IIs recognition sequence and the tag sequence is 3' of the common sequence. In many embodiments there will be one or more mismatches between the probe and the target at the site of the Type IIs site. In some embodiments the Type IIs site is positioned so that when the fragment is digested the enzyme cuts between the polymorphic position and the base just 5' of the polymorphic position. The nucleic acid sample is fragmented and ligated to adapters comprising a second common sequence. The capture probes and adapter-ligated fragments are mixed under conditions that allow hybridization and the capture probes are extended. The extended capture probes are then made double stranded using a primer that is complementary to the adapter. The double stranded extended capture probes are amplified using primers to the common sequence in the capture probe and the common sequence in the adapter.

To detect the allele or alleles present the amplified fragments are digested with a Type IIs restriction endonuclease and the fragments (FIG. 4b) are extended in the presence of labeled ddNTPs. The fragments will be extended by a single ddNTP which corresponds to the allele present at the polymorphic position. The extended fragments are hybridized to an array of tag probes and the labeled nucleotide or nucleotides present at each location are determined. In one embodiment the ddNTPs are all labeled with the same label, for example, biotin and the fragments are extended in four separate reactions, one for each of the four different ddNTPs. Each reaction is hybridized to a different array so four arrays are used. In another embodiment the ddNTPs are labeled with differentially detectable labels. In one embodiment there are four different labels and the extension reaction may be done in a single reaction and the hybridization may be to a single array. In another embodiment there are two different labels and extension reaction may be done in two reactions and the hybridization may be to two different arrays.

Figure 5:
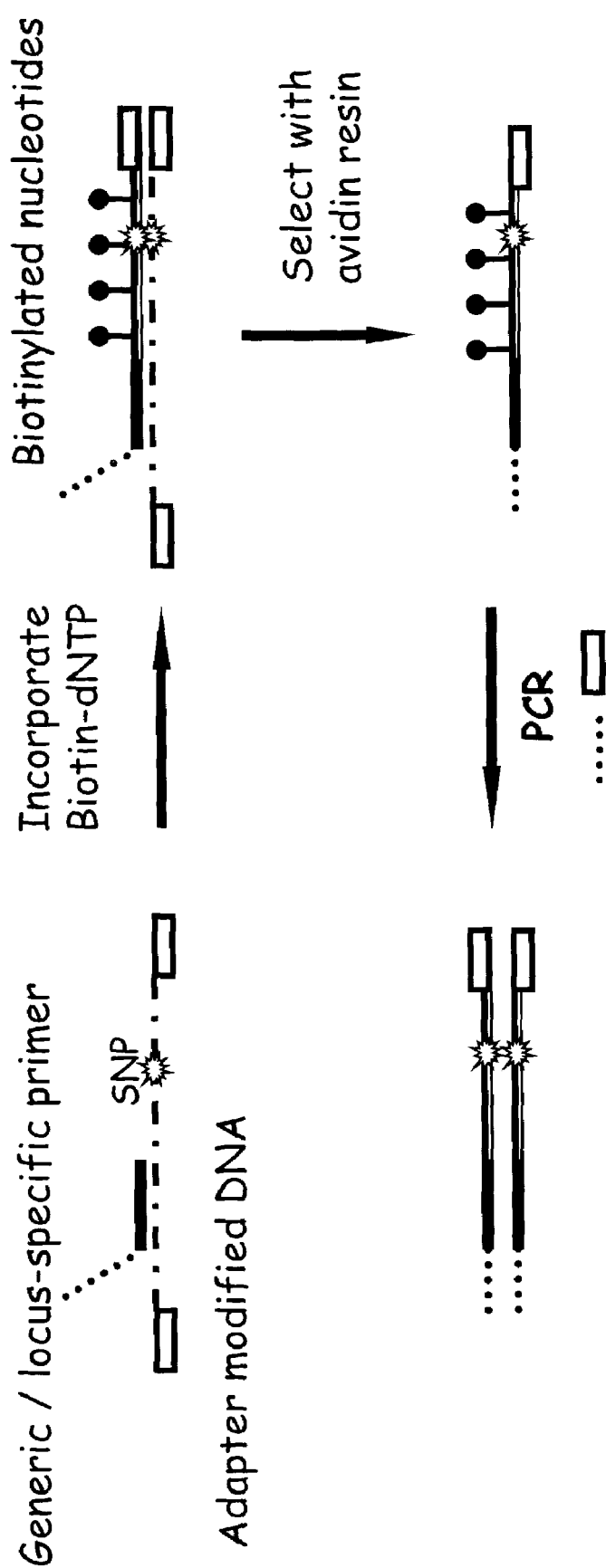
FIG. 5 shows an enrichment scheme. Biotin is incorporated into the extended capture probes and biotin labeled extended capture probes are selected by affinity chromatography.
Figure 6:
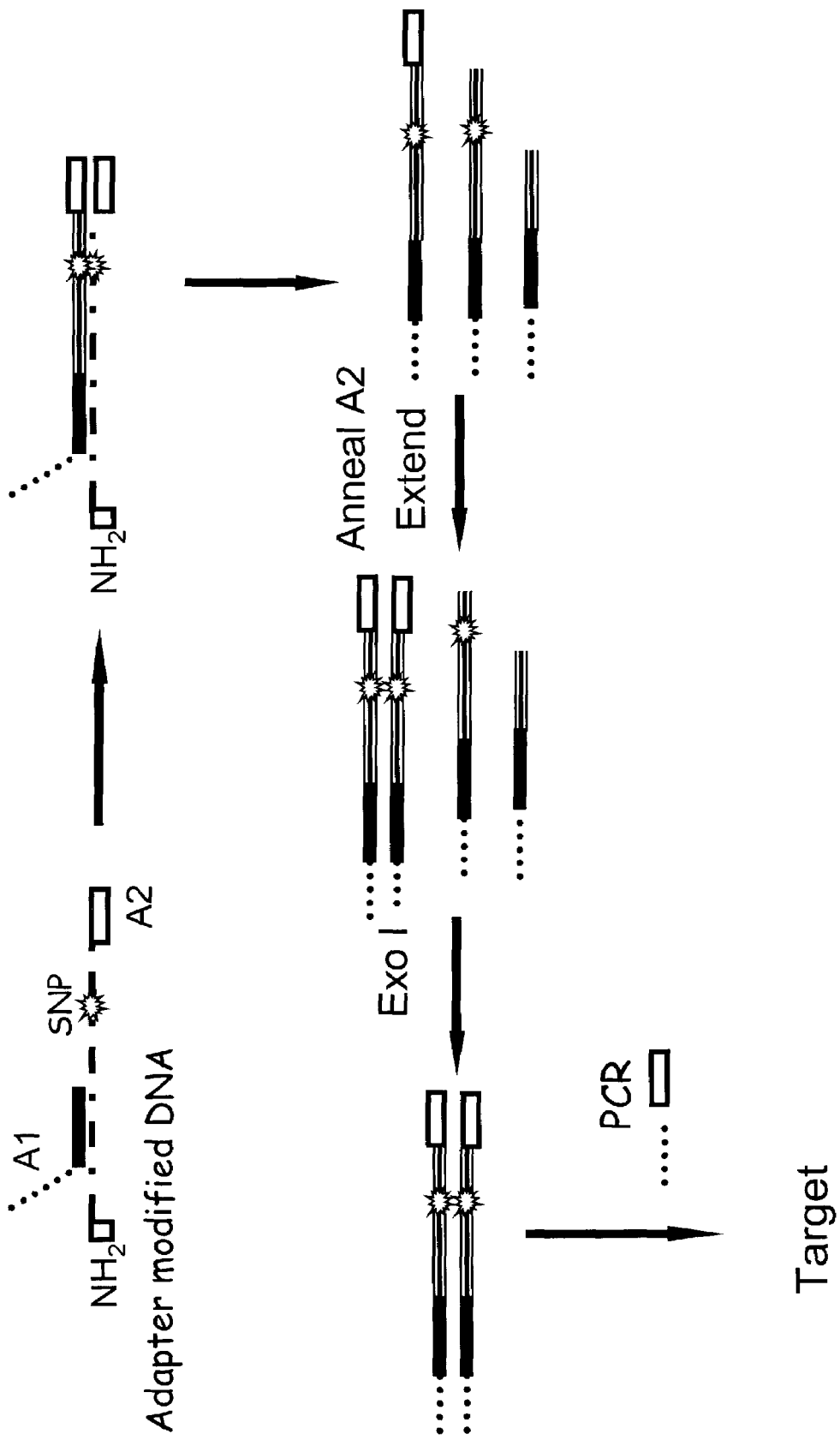
FIG. 6 shows another enrichment scheme using nuclease that is specific for single stranded nucleic acid. Capture probes that are fully extended through the adapter site on the genomic DNA fragment are converted to double stranded DNA by annealing and extension of a primer that hybridizes to the adapter sequence.

In many embodiments of the present methods one or more enrichment step may be included to generate a sample that is enriched for extended capture probes prior to amplification with common sequence primers (see, FIGS. 5–7). In some embodiments it is desirable to separate extended capture probes from fragments from the starting nucleic acid sample, adapter-ligated fragments, adapter sequences or non-extended capture probes, for example. In one embodiment (FIG. 5) the capture probes are extended in the presence of a labeled dNTP, for example dNTPs labeled with biotin. The labeled nucleotides are incorporated into the extended capture probes and the labeled extended capture probes are then separated from non-extended material by affinity chromatography. When the label is biotin the labeled extended capture probes can be isolated based on the affinity of biotin for avidin, streptavidin or a monoclonal anti-biotin antibody. In one embodiment the antibody may be coupled to protein-A agarose, protein-A sepharose or any other suitable solid support known in the art. Those of skill in the art will appreciate that biotin is one label that may be used but any other suitable label or a combination of labels may also be used, such as fluorescein which may be incorporated in the extended capture probe and an anti-fluorescein antibody may be used for affinity purification of extended capture probes. Other labels such as, digoxigenin, Cyanine-3, Cyanine-5, Rhodamine, and Texas Red may also be used. Antibodies to these labeling compounds may be used for affinity purification. Also, other haptens conjugated to dNTPs may be used, such as, for example, dinitrophenol (DNP).

In another embodiment (FIG. 6) capture probes that have been extended through the adapter sequence (A2) on the adapter modified DNA are made double stranded by hybridizing and extending A2 primer. Only the fully extended capture probes will have the A2 priming site so partially extended capture probes will remain single-stranded. The sample is then digested with a nuclease that selectively digests single stranded nucleic acid, such as E. Coli Exonuclease I. The sample is then amplified with primers A1 and A2.

In another embodiment (FIG. 7) extension products may be enriched by circularization followed by digestion with a nuclease such as Exonuclease VII or Exonuclease III. The extended capture probes may be circularized, for example, by hybridizing the ends of the extended capture probe to an oligonucleotide splint so that the ends are juxtaposed and ligating the ends together. The splint will hybridize to the A1 and A2 sequences in the extended capture probe and bring the 5' end of the capture probe next to the 3' end of the capture probe so that the ends may be ligated by a ligase, for example DNA Ligase or Ampligase Thermostable DNA. See, for example, U.S. Pat. No. 5,871,921 which is incorporated herein by reference. The circularized product will be resistant to nucleases that require either a free 5' or 3' end.

A variety of nucleases may be used in one or more of the embodiments. Nucleases that are commercially available and may be useful in the present methods include: Mung Bean Nuclease, E. Coli Exonuclease I, Exonuclease III, Exonuclease VII, T7 Exonuclease, BAL-31 Exonuclease, Lambda Exonuclease, RecJ$_f$, and Exonuclease T. Different nucleases have specificities for different types of nucleic acids making them useful for different applications. Exonuclease I catalyzes the removal of nucleotides from single-stranded DNA in the 3' to 5' direction. Exonuclease I degrades excess single-stranded primer oligonucleotide from a reaction mixture containing double-stranded extension products. Exonuclease III catalyzes the stepwise removal of mononucleotides from 3'-hydroxyl termini of duplex DNA. A limited number of nucleotides are removed during each binding event, resulting in coordinated progressive deletions within the population of DNA molecules. The preferred substrates are blunt or recessed 3'-termini, although the enzyme also acts at nicks in duplex DNA to produce single-strand gaps. The enzyme is not active on single-stranded DNA, and thus 3'-protruding termini are resistant to cleavage. The degree of resistance depends on the length of the extension, with extensions 4 bases or longer being essentially resistant to cleavage. This property can be exploited to produce unidirectional deletions from a linear molecule with one resistant (3'-overhang) and one susceptible (blunt or 5'-overhang) terminus. Exonuclease VII is a single-strand directed enzyme with 5' to 3'- and 3' to 5'-exonuclease activities making it the only bi-directional E. coli exonuclease with single-strand specificity. The enzyme has no apparent requirement for divalent cation, and is fully active in the presence of EDTA. Initial reaction products are acid-insoluble oligonucleotides which are further hydrolyzed into acid-soluble form. The products of limit digests are small oligomers (dimers to dodecamers). For additional information about nucleases see catalogues from manufacturers such as New England Biolabs, Beverly, Mass.

In some embodiments one of the primers added for PCR amplification is modified so that it is resistant to nuclease digestion, for example, by the inclusion of phosphorothioate. Prior to hybridization to an array one strand of the double stranded fragments may be digested by a 5' to 3' exonuclease such as T7 Gene 6 Exonuclease.

In some embodiments the nucleic acid sample, which may be, for example, genomic DNA, is fragmented, using for example, a restriction enzyme, DNase I or a non-specific fragmentation method such as that disclosed in U.S. patent application Ser. No. 09/358,664, which is incorporated herein by reference in its entirety. Adapters containing at least one priming site are ligated to the fragmented DNA. Locus-specific primers are synthesized which contain a different adapter sequence at the 5' end. The adapter-ligated genomic DNA is hybridized to the locus-specific primers and the locus specific primer is extended. This may be done for example, by the addition of DNA polymerase and dNTPs. Extension products may be amplified with primers that are specific for the adapter sequences. This allows amplification of a collection of many different sequences using a limited set of primers. For example, a single set of primers may be used for amplification. In another embodiment a second amplification step is carried out using the same or different primers.

In some embodiments the amplified products are analyzed by hybridization to an array of probes attached to a solid support. In some embodiments an array of probes is specifically designed to interrogate a collection of target sequences. The array of probes may interrogate, for example, from 1,000, 5,000, 10,000 or 100,000 to 2,000, 5,000, 10,000, 100,000, 1,000,000 or 3,000,000 different target sequences. In one embodiment the target sequences contain SNPs and the array of probes is designed to interrogate the allele or alleles present at one or more polymorphic location. The array may comprise a collection of probes that hybridize specifically to one or more SNP containing sequences. The array may comprise probes that correspond to different alleles of the SNP. One probe or probe set may hybridize specifically to a first allele of a SNP, but not hybridize significantly to other alleles of the SNP and a second probe set may be designed to hybridize to a second allele of a SNP but not hybridize significantly to other alleles. A hybridization pattern from the array indicates which of the alleles are present in the sample. An array may contain probe sets to interrogate, for example, from 1,000, 5,000, 10,000 or 100,000 to 2,000, 5,000, 10,000, 100,000, 1,000,000 or 3,000,000 different SNPs.

In another embodiment an array of probes that are complementary to tag sequences present in the capture probes is used to interrogate the target sequences. In some embodiments the amplified targets are analyzed on an array of tag sequences, for example, the Affymetrix GenFlex® array (Affymetrix, Inc., Santa Clara, Calif.). In this embodiment the capture probes comprise a tag sequence that is unique for each species of capture probe. A detectable label that is indicative of the allele present at the polymorphic site of interest is associated with the tag. The labeled tags are hybridized to the one or more arrays and the hybridization pattern is analyzed to determine which alleles are present.

In another embodiment methods for generating a plurality of different oligonucleotides are disclosed. Oligonucleotides are synthesized in parallel on a solid support. The oligonucleotides are then released from the solid support and used for further analysis. The released probes may be used, for example, for multiplex PCR amplification of a collection of target sequences, for probes, for primers for reverse transcription or amplification or for any other use of oligonucleotides known in the art. In one embodiment the oligonucleotides on the solid support comprise a collection of capture probes.

In another embodiment kits that are useful for the present methods are disclosed. In one embodiment a kit for amplifying a collection of target sequences is disclosed. The kit may comprise one or more of the following: a collection of capture probes as disclosed, one or more adapter, one or more generic primers for common sequences, one or more restriction enzymes, buffer, one or more polymerase, a ligase, buffer, dNTPs, ddNTPs, and one or more nucleases. The restriction enzyme of the kit may be a type-IIs enzyme. The capture probes may be attached to a solid support.

Methods of Use

The methods of the presently claimed invention can be used for a wide variety of applications. Any analysis of genomic DNA may be benefited by a reproducible method of complexity management. Furthermore, the methods and enriched fragments of the presently claimed invention are particularly well suited for study and characterization of extremely large regions of genomic DNA.

In a preferred embodiment, the methods of the presently claimed invention are used for SNP discovery and to genotype individuals. For example, any of the procedures described above, alone or in combination, could be used to isolate the SNPs present in one or more specific regions of genomic DNA. Selection probes could be designed and manufactured to be used in combination with the methods of the invention to amplify only those fragments containing regions of interest, for example a region known to contain a SNP. Arrays could be designed and manufactured on a large scale basis to interrogate only those fragments containing the regions of interest. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, in U.S. Pat. No. 6,361,947 and co-pending U.S. application Ser. No. 08/813,159 which are herein incorporated by reference in their entirety for all purposes).

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000–2,000 bases when two human chromosomes are compared. (See, The International SNP Map Working Group, *Science* 409: 928–933 (2001) incorporated herein by reference in its entirety for all purposes.) Human diversity is limited not only by the number of SNPs occurring in the genome but further by the observation that specific combinations of alleles are found at closely linked sites.

Correlation of individual polymorphisms or groups of polymorphisms with phenotypic characteristics is a valuable tool in the effort to identify DNA variation that contributes to population variation in phenotypic traits. Phenotypic traits include physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531–537 (2001) hereby incorporated by reference in its entirety for all purposes.)

Pharmacogenomics

Pharmacogenomics refers to the study of how genes affect response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, *Science* 286: 487–491 (2001) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharamaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures. Paternity testing is commonly used to establish a biological relationship between a child and the putative father of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. *Nature Genet.* 22, 78 (1999)).

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual.

Marker Assisted Breeding

Genetic markers can assist breeders in the understanding, selecting and managing of the genetic complexity of animals and plants. Agriculture industry, for example, has a great deal of incentive to try to produce crops with desirable traits (high yield, disease resistance, taste, smell, color, texture, etc.) as consumer demand increases and expectations change. However, many traits, even when the molecular mechanisms are known, are too difficult or costly to monitor during production. Readily detectable polymorphisms which are in close physical proximity to the desired genes can be used as a proxy to determine whether the desired trait is present or not in a particular organism. This provides for an efficient screening tool which can accelerate the selective breeding process.

EXAMPLES

Example 1

Multiplexed Anchored Runoff Amplification

Genomic DNA was digested with MseI and ligated to an adapter containing T7 promoter sequence as a priming site. The final concentration of the genomic DNA was 10 ng/µl in 1× T4 DNA Ligase Buffer. To generate extended capture probes 2.5 µl of adapter ligated DNA, 2.5 µl 10× Taq Gold Buffer, 2 µl 25 mM MgCl2, 2.5 µl 10× dNTPs, 5 µl of a 500 nM mixture of 150 different capture probes in TE buffer corresponding to 150 different forward primers from the HuSNP assay, 0.25 µl Perfect Match Enhancer, 0.25 µl AmpliTaq Gold (Applied Biosystems, Foster City, Calif.) and 10 µl of water were mixed to give a final reaction volume of 25 µl. The reaction was incubated at 95° C. for 6 min followed by 26 cycles of 95° C. for 30 sec, 68° C. for 2.5 min (decreasing 0.5° C. on each subsequent cycle) and 72° C. for 1 min, then to 4° C.

The extended capture probes were made double stranded by the addition of 0.25 µl of 1 µM T7 primer and incubation at 95° C. for 2 min, 55° C. for 2 min, 72° C. for 6 min, then to 4° C. The reaction was passed over a G-25 Sephadex column and 5 µl of 10× Exonuclease I Buffer (NEB) and 2 µl of Exonuclease I (NEB) were added and the reaction was incubated at 37° C. for 60 min, 80° C. for 20 min, then to 4° C. The products were purified over a Qiagen (Valencia, Calif.) mini-elute column and eluted with 10 µl EB Buffer.

Generic PCR was done as follows: 65.5 µl water, 10 µl 10× Taq Gold Buffer, 8 µl 25 mM MgCl2, 10 µl 10×dNTPs, 1 µl 1 µM T3 primer, 1 µl 1 µM T7 primer 3 µl DNA, 0.5 µl Perfect Match Enhancer and 1 µl AmpliTaq Gold were mixed in a 100 µl final reaction volume and incubated at 95° C. for 8 min, 40 cycles of 95° C. for 30 sec, 55° C. for 1 min, and 72° C. for 1 min, then 72° C. for 6 min followed and finally to 4° C.

An aliquot of the reaction was analyzed on a 2% agarose gel. The products were concentrated using Qiagen QIAquick columns and eluted with 10 µl EB Buffer. The products were fragmented, labeled and hybridized to an array under standard conditions and hybridization patterns were analyzed.

Example 2

Multiplexed Anchored Runoff Amplification with Biotin Enrichment

Prepare adaptor ligated genomic DNA as above. To generate extended capture probes 2.5 µl of adapter ligated DNA, 2.5 µl 10× Taq Gold Buffer, 2 µl 25 mM MgCl$_2$, 0.5 µl 50×acGT (6 mM dATP, 6 mM dCTP, 10 mM dGTP, 10 mM dTTP), 5 µl of a 500 nM mixture of 150 different capture probes in TE buffer corresponding to 150 different forward primers from the HuSNP assay, 0.25 µl Perfect Match Enhancer, 0.25 µl Amplitaq Gold, 2 µl 1 mM Biotin-N6-dATP (Perkin Elmer, Boston, Mass.), 2 µl 1 mM Biotin-N4-dCTP (Perkin Elmer) and 8 µl of water were mixed to give a final reaction volume of 25 µl. The reaction was incubated at 95° C. for 6 min followed by 26 cycles of 95° C. for 30 sec, 68° C. for 2.5 min (decreasing 0.5° C. on each subsequent cycle) and 72° C. for 1 min, then to 4° C. Pass reaction over G-25 Sephadex column to remove unincorporated biotin-dNTPs.

Enrich for biotinylated extension products. Adjust the G-25 eluate to 1×PCR buffer and 2 mM MgCl$_2$. Add 15 µl monoclonal anti-biotin agarose (Clone BN-34, Sigma). Incubate at room temperature for 30 min with gentle agitation. Spin down agarose resin for 3 min at 5,000 rpm. Aspirate away supernatant and wash agarose resin with 250 µl 1×PCR buffer with 2 mM MgCl$_2$. Aliquot agarose resin into PCR tubes for generic PCR with T3 and T7 primers.

Generic PCR was done as follows: 65.5 µl water, 10 µl 10× Taq Gold Buffer, 8 µl 25 mM MgCl$_2$, 10 µl 10×dNTPs, 1 µl 1 µM T3 primer, 1 µl 1 µM T7 primer, 3 µl DNA, 0.5 µl Perfect Match Enhancer and 1 µl AmpliTaq Gold were mixed in a 100 µl final reaction volume and incubated at 95° C. for 8 min, 40 cycles of 95° C. for 30 sec, 55° C. for 1 min, and 72° C. for 1 min, then 72° C. for 6 min and finally to 4° C.

An aliquot of the reaction was analyzed on a 2% agarose gel. The products were concentrated using Qiagen QIAquick columns and eluted with 30 µl EB Buffer. The products were fragmented with DNase I, labeled with biotin-ddATP using TdT, and hybridized to an array under standard conditions. Hybridization patterns were analyzed.

Example 3

Multiplexed Anchored Runoff Amplification with Exo III Enrichment

Prepare adaptor ligated genomic DNA as above. Kinase capture probes by incubating 12 µl of a 150-plex stock of either forward or reverse HuSNP® primers with 12.7 µl H₂O, 3 µl 10× T4 polynucleotide kinase buffer, 0.3 µl 100 mM ATP, and 2 µl T4 Polynucleotide Kinase. Incubate the reaction at 37° C. for 30 min. Adjust reaction volume to 50 µl and pass reaction over G-25 column to exchange buffer.

To generate extended capture probes 5 µl of adapter ligated DNA, 5 µl 10× Taq Gold Buffer, 4 µl 25 mM MgCl₂, 5 µl 10×dNTPs, 20 µl of the kinased mixture of 150 different capture probes, 1 µl Perfect Match Enhancer, 0.5 µl AmpliTaq Gold and 9.5 µl of water were mixed to give a final reaction volume of 50 µl. The reaction was incubated at 95° C. for 6 min followed by 26 cycles of 95° C. for 30 sec, 68° C. for 2.5 min (decreasing 0.5° C. on each subsequent cycle) and 72° C. for 1 min, then finally to 4° C. Pass the reaction over a G-25 column to exchange buffer.

Convert the single strand extension products to single strand circles using splint oligonucleotides and Ampligase Thermostable DNA Ligase (Epicenter, Madison, Wis.). The sequence of the T3-T7 splint oligo is (SEQ ID NO: 3) 5'TCTCCCTTTAGTGAGGGTTAATTTG-TAATACGACTCACTATAGGGCA-3'. Mix 39.75 µl water, 7.5 µl 10× Ampligase Buffer, 1.25 µl 70 µM splint oligo, 25 µl 5' phosphorylated single strand extension products and 1.5 µl Ampligase Thermostable DNA Ligase 5 U/µl. Incubate the mixture at 95° C. for 3 min, then 10 cycles of 95° C. for 30 sec and 72° C. for 3 min, then 10 cycles of 95° C. for 30 sec and 70° C. for 3 min, then 10 cycles of 95° C. for 30 sec and 68° C. for 3 min, then 10 cycles of 95° C. for 30 sec and 66° C. for 3 min, then 10 cycles of 95° C. for 30 sec and 64° C. for 3 min, then 10 cycles of 95° C. for 30 sec and 62° C. for 3 min. Hold at 4° C. Pass reaction over G-25 column to exchange buffer.

Digest uncircularized nucleic acids. Mix 13 µl water, 10 µl 10× Exo III Buffer, 75 µl Ampligase/splint reaction and 2 µl Exonuclease III 100 U/µl (NEB, Beverly, Mass.). Incubate at 37° C. for 1 hour. Heat inactivate at 70° C. for 20 min. Fragment, label and hybridize as above.

CONCLUSION

From the foregoing it can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

We claim:

1. A method for genotyping one or more polymorphisms in a nucleic acid sample comprising:
   fragmenting the nucleic acid sample to generate fragments;
   ligating an adapter to the fragments said adapter comprising a first priming sequence;
   hybridizing a collection of capture probes to the fragments, wherein said capture probes comprise in the following order from 5' to 3': a second priming sequence that is common to the capture probes in the collection, a tag sequence unique for each species of capture probe, a first target specific sequence, a Type IIs restriction enzyme recognition sequence, and a second target specific sequence wherein the Type IIs restriction enzyme recognition sequence is positioned so that the enzyme will cut on the 5' side of a polymorphic base;
   extending said capture probes to generate extended capture probes in a first extension reaction;
   amplifying the extended capture probes with primers to said first and second priming sequences;
   digesting the amplified product with a Type IIs restriction enzyme to generate amplified product fragments;
   extending the amplified product fragments in at least one second extension reaction;
   hybridizing each second extension reaction to an array comprising tag probes that hybridize to the tag sequences in the capture probes; and
   analyzing the hybridization pattern on each of the arrays to determine the genotype of one or more polymorphisms in the nucleic acid sample.

2. The method of claim 1 wherein in each second extension reaction there is at least one species of labeled ddNTP.

3. The method of claim 2 wherein one or more species of ddNTPs is labeled with biotin.

4. The method of claim 2 wherein there are four separate second extension reactions wherein each second extension reaction contains a different species of labeled ddNTP and the extension reaction products from each second extension reaction are hybridized to a different array.

5. The method of claim 2 wherein there are two separate second extension reactions wherein two differentially labeled ddNTPs are present in each second extension reaction and the second extension reaction products are hybridized to a different array.

6. The method of claim 2 wherein there is one second extension reaction wherein four differentially labeled ddNTPs are present in the second extension reaction and the extension reaction products are hybridized to a single array.

7. The method of claim 2 wherein said capture probes are attached to a solid support.

8. The method of claim 7 wherein said capture probes are attached to the solid support through a covalent interaction.

9. The method of claim 7 wherein said capture probes are attached to said solid support by hybridization to a collection of tag probes that are attached to said solid support.

10. The method of claim 7 wherein each species of capture probe is attached to said solid support in a discrete location.

11. The method of claim 7 wherein said capture probes are synthesized on a solid support in a 5' to 3' direction.

12. The method of claim 1 wherein one of the primers to said first and second priming sequences is resistant to nuclease digestion and each second extension reaction is digested with a 5' to 3' nuclease activity prior to hybridization to an array.

13. The method of claim 12 wherein the nuclease resistant primer comprises phosphorothioate linkages.

14. The method of claim 12 wherein said nuclease is T1 Gene 6 Exonuclease.

15. The method of claim 1 wherein prior to amplification, the extended capture probes are enriched in the sample to be amplified, wherein the method of enrichment comprises depletion of non-extended products or positive selection of extended products.

16. The method of claim 1 wherein labeled nucleotides are incorporated into the extended capture probes and extended capture probes are isolated by affinity chromatography.

17. The method of claim 16 wherein said labeled nucleotides are labeled with biotin, wherein avidin, streptavidin or an anti-biotin antibody is used to isolate extended capture probes.

18. The method of claim 1 wherein prior to amplification, the extended capture probes are circularized and uncircularized nucleic acid in the sample is digested.

19. The method of claim 18 wherein extended capture probes are circularized by a method comprising:
hybridizing an oligonucleotide splint to the extended capture probes, wherein the oligonucleotide splint is complementary to the first and second priming sequences, thereby juxtaposing the 5' and 3' ends of extended capture probes; and
ligating the ends of the extended capture probes to form circular extended capture probes.

20. The method of claim 18 wherein the uncircularized nucleic acid remaining in the sample is digested with a nuclease.

21. The method of claim 20 wherein the nuclease is Exonuclease III.

22. The method of claim 1 wherein the nucleic acid sample is fragmented by digestion with one or more restriction enzymes.

23. The method of claim 1 wherein there are 100 to 1500 different target sequences in the collection of target sequences.

24. The method of claim 1 wherein there are 1,000 to 5,000 different target sequences in the collection of target sequences.

25. The method of claim 1 wherein there are 2,000 to 10,000 different target sequences in the collection of target sequences.

26. The method of claim 1 wherein there are 10,000 to 1,000,000 different target sequences in the collection of target sequences.

27. A method for screening for sequence variations in a population of individuals comprising:
providing a nucleic acid sample from each individual;
determining the genotype of one or more polymorphisms in each sample according to the method of claim 1; and
comparing the genotypes from the samples to determine the presence or absence of sequence variation in the population of individuals.

* * * * *

SEQUENCE LISTING

```
<160> NUMBER OF SEQ ID NOS: 12

<210> SEQ ID NO 1
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

<400> SEQUENCE: 1
ctcttcnnnn n                                                        11

<210> SEQ ID NO 2
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, c, g, or t

<400> SEQUENCE: 2
nnnnngaaga g                                                        11

<210> SEQ ID NO 3
<211> LENGTH: 47
```

```
<212> TYPE: DNA
<213> ORGANISM: Artificial Sequence
<220> FEATURE:
<223> OTHER INFORMATION: Synthetic

<400> SEQUENCE: 3
tctcccttta gtgagggtta atttgtaata cgactcacta tagggca                      47

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4
aagattctaa taacctcgca gcgtgaaaac                                         30

<210> SEQ ID NO 5
<211> LENGTH: 37
<212> TYPE: DNA
<213> ORGANISM: Artificial Sequence
<220> FEATURE:
<223> OTHER INFORMATION: Synthetic

<400> SEQUENCE: 5
cttttttgag gcatgttmgt tttcacctta agaggtt                                 37

<210> SEQ ID NO 6
<211> LENGTH: 48
<212> TYPE: DNA
<213> ORGANISM: Artificial Sequence
<220> FEATURE:
<223> OTHER INFORMATION: Synthetic

<400> SEQUENCE: 6
aagattctaa taacctcgca gcgtgaaaac kaacatgcct caaaaaag                     48

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7
aagattctaa taacctcgca gcgtgaaaac kaacatgcct caaaaaag                     48

<210> SEQ ID NO 8
<211> LENGTH: 48
<212> TYPE: DNA
<213> ORGANISM: Artificial Sequence
<220> FEATURE:
<223> OTHER INFORMATION: Synthetic

<400> SEQUENCE: 8
cttttttgag gcatgttmgt tttcacgctg cgaggttatt agaatctt                     48

<210> SEQ ID NO 9
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (75)..(79)
```

-continued

<223> OTHER INFORMATION: n is a, c, g, or t

<400> SEQUENCE: 9
aattaaccct cactaaaggg agacgttcct aaagctgagt ctgaagattc taataacctc    60
gcagcgtgaa aacknnnnn                                                79

<210> SEQ ID NO 10
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, c, g, or t

<400> SEQUENCE: 10
nnnnnmgttt tcacgctgcg aggttattag aatcttcaga ctcagcttta ggaacgtctc    60
cctttagtga gggttaatt                                                79

<210> SEQ ID NO 11
<211> LENGTH: 73
<212> TYPE: DNA
<213> ORGANISM: Artificial Sequence
<220> FEATURE:
<223> OTHER INFORMATION: Synthetic

<400> SEQUENCE: 11
aattaaccct cactaaaggg agacgttcct aaagctgagt ctgaagattc taataacctc    60
gcagcgtgaa aac                                                      73

<210> SEQ ID NO 12
<211> LENGTH: 74
<212> TYPE: DNA
<213> ORGANISM: Artificial Sequence
<220> FEATURE:
<223> OTHER INFORMATION: Synthetic

<400> SEQUENCE: 12
aattaaccct cactaaaggg agacgttcct aaagctgagt ctgaagattc taataacctc    60
gcagcgtgaa aack                                                     74